US012565678B2

(12) United States Patent
Fretes

(10) Patent No.: US 12,565,678 B2
(45) Date of Patent: Mar. 3, 2026

(54) GRAPHENE NANOPORE DEVICE FOR SEQUENCING NUCLEIC ACIDS

(71) Applicant: Gentroma Inc., Flushing, NY (US)

(72) Inventor: Krista Fretes, New York, NY (US)

( * ) Notice: Subject to any disclaimer, the term of this patent is extended or adjusted under 35 U.S.C. 154(b) by 1038 days.

(21) Appl. No.: 17/606,919

(22) PCT Filed: Apr. 29, 2020

(86) PCT No.: PCT/US2020/030349
§ 371 (c)(1),
(2) Date: Oct. 27, 2021

(87) PCT Pub. No.: WO2020/223271
PCT Pub. Date: Nov. 5, 2020

(65) Prior Publication Data
US 2022/0235415 A1 Jul. 28, 2022

Related U.S. Application Data

(60) Provisional application No. 62/841,201, filed on Apr. 30, 2019.

(51) Int. Cl.
*C12Q 1/6874* (2018.01)
*G01N 27/327* (2006.01)
*G01N 33/487* (2006.01)

(52) U.S. Cl.
CPC ..... *C12Q 1/6874* (2013.01); *G01N 33/48721* (2013.01)

(58) Field of Classification Search
CPC ................................................ G01N 33/48721
See application file for complete search history.

(56) References Cited

U.S. PATENT DOCUMENTS

| | | | | |
|---|---|---|---|---|
| 6,267,872 B1 * | 7/2001 | Akeson | ................ | C12Q 1/6869 |
| | | | | 977/932 |
| 2004/0229386 A1 * | 11/2004 | Golovchenko | .. | G01N 33/48721 |
| | | | | 438/10 |

(Continued)

FOREIGN PATENT DOCUMENTS

WO      WO 2011143340 A2 *  11/2011   ............... C12Q 1/68

OTHER PUBLICATIONS

Wu et al., "Fabrication of nanopore in graphene by electron and ion beam irradiation: Influence of graphene thickness and substrate," Computational Materials Science 102 (2015) 258-266 (Year: 2015).*

(Continued)

*Primary Examiner* — Alexander S Noguerola
(74) *Attorney, Agent, or Firm* — FRESH IP PLC; Michael Anderson

(57) ABSTRACT

A nano-sensing device is disclosed for high throughput nucleic acid sequencing. The device is a silicon chip, having a silicon substrate with a groove or well, a microfluidic channel, and a polarized multilayer graphene sheet with nanopores about 0.3 to 3.0 nm wide. A base substrate layer of silicon nitride, alumina, or boron nitride may be employed. Ionic forces cause a nucleic acid strand to translocate through the nanopore. The specific nucleobases comprising the nucleic acid can be detected and assigned using localized surface plasmonic resonance (LSPR) and laser or diode light source and optical detector. Alternatively, nucleobases translocating through the nanopores can be detected and assigned by ionic current detection with a patch-clamp amplifier. Also disclosed are arrays of inventive devices.

6 Claims, 13 Drawing Sheets

(56)        References Cited

U.S. PATENT DOCUMENTS

| | | | |
|---|---|---|---|
| 2011/0193570 A1* | 8/2011 | Chen ............... | G01N 33/48721 |
| | | | 324/654 |
| 2014/0174927 A1 | 6/2014 | Bashir et al. | |
| 2015/0069329 A1* | 3/2015 | Jeon .................... | B81C 1/00087 |
| | | | 257/29 |

OTHER PUBLICATIONS

Kirilenko et al., "Measuring the corrugation amplitude of suspended and supported graphene," Physical Review B 84, 235417 (2011) (Year: 2011).*

Li, R., Kothari, M., Landauer, A., Cha, M., Kwon, H., & Kim, K. (2018). A New Subcritical Nanostructure of Graphene—Crinkle-Ruga Structure and Its Novel Properties. MRS Advances, 3(45-46), 2763-2769. doi:10.1557/adv.2018.432.

Traversi, F., Raillon, C., Benameur, S. et al. Detecting the translocation of DNA through a nanopore using graphene nanoribbons. Nature Nanotech 8, 939-945 (2013). https://doi.org/10.1038/nnano.2013.240.

https://en.wikipedia.org/wiki/Nanopore_sequencing (downloaded Oct. 18, 2021) (cited in ISR).

International Search Report issued Sep. 28, 2020 in PCT/US2020/030349.

Deamer, D. W., and Branton, D. (2002). Characterization of nucleic acids by nanopore analysis. Acc. Chem. Res. 35, 817-825. doi:10.1021/ar000138m.

Derrington, I. M., Butler, T. Z., Collins, M. D., Manrao, E., Pavlenok, M., Niederweis, M., et al. (2010). Nanopore DNA sequencing with MspA. Proc. Natl. Acad. Sci. U.S.A. 107, 16060-16065. doi: 10.1073/pnas.1001831107.

Yanxiao Feng, Yuechuan Zhang, Cuifeng Ying, Deqiang Wang, Chunlei Du., "Nanopore-based Fourth-generation DNA Sequencing Technology," Genomics, Proteomics & Bioinformatics, 2015, 13(1) 4-16; https://doi.org/10.1016/j.gpb.2015.01.009; erratum 2015, 13 (6) 383, https://doi.org/10.1016/j.gpb.2016.01.001.

Daniel J Giguere, Alexander T Bahcheli, Benjamin R Joris, Julie M Paulssen, Lisa M Gieg, Martin W Flatley, Gregory B Gloor; Complete and validated genomes from a metagenome, bioRxiv 2020.04.08.032540; doi: https://doi.org/10.1101/2020.04.08.032540.

Kim, K-S et al., "A New Subcritical Nanostructure of Graphene-Crinkle-Ruga Structure and Its Novel Properties," MRS Advances, 2018, 3(45-46) (Nanomaterials), 2763-2769, https://doi.org/10.1557/adv.2018.432.

S. Liu, Q. Zhao, J. Xu, K. Yan, H.L. Peng, F.H. Yang, et al., "Fast and controllable fabrication of suspended graphene nanopore devices," Nanotechnology 2012, 23(8), 085301. doi: 10.1088/0957-4484/23/8/085301. Epub Feb. 1, 2012.

Rang, F.J., Kloosterman, W.P. & de Ridder, J. From squiggle to basepair: computational approaches for improving nanopore sequencing read accuracy. Genome Biol 19, 90 (2018). https://doi.org/10.1186/s13059-018-1462-9.

Smolyanitsky, A. et al. "Nucleobase-functionalized graphene sheets for accurate high-speed DNA sequencing," Nanoscale, 2016, 8, 1861-1867, https://doi.org/10.1039/C5NR07061A.

B.M. Venkatesan, B. Dorvel, S. Yemenicioglu, N. Watkins, I. Petrov, R. Bashir, "Highly sensitive, mechanically stable nanopore sensors for DNA analysis" Adv. Mater., 2009, 21, 2771-2776. doi:10.1002/adma.200803786.

Verschueren DV, Pud S, Shi X, De Angelis L, Kuipers L, Dekker C. "Label-Free Optical Detection of DNA Translocations through Plasmonic Nanopores" ACS Nano. Jan. 22, 2019;13(1):61-70. doi: 10.1021/acsnano.8b06758. Epub Dec. 4, 2018. PubMed PMID: 30512931; PubMed Central PMCID: PMC6344913.

Wang, Yue et al. "The evolution of nanopore sequencing." Frontiers in genetics vol. 5 449. Jan. 7, 2015, doi:10.3389/fgene.2014.00449.

Nanopore Sequencing—Wikipedia—https://en.wikipedia.org/wiki/Nanopore_sequencing.

ISR in PCT/US2020/30349 issued on Sep. 28, 2020.

WOSA in PCT/US2020/30349 issued on Sep. 28, 2020.

Notification of the Second Office Action for China Patent Application No. 202080038595.3, mailing date of Apr. 28, 2025.

First Examination Opinion Notice for China Patent Application No. 202080038595.3, mailing date of Jul. 18, 2024.

* cited by examiner

GRAPHENE NANOPORE DEVICE FOR SEQUENCING NUCLEIC ACIDS

CROSS REFERENCE TO RELATED APPLICATION

This patent application claims priority to U.S. patent application 62/841,201, filed Apr. 30, 2019, the contents of which are incorporated by reference.

FIELD OF THE INVENTION

This invention pertains to DNA sequencing using a chip employing a subcritical multilayer graphene nanostructure and optionally Localized Surface Plasmon Resonance.

BACKGROUND

Generations of DNA sequencing technologies, from Sanger sequencing to nanopore sequencing, have been developed to address the important applications of genetic sequencing, of which the most essential is personalized medicine for a e.g., cancer, genetic disorders, and complex disease treatments. Additional applications that also require efficient DNA sequencing platforms include vaccine research, epidemic prevention, food monitoring, forensic sample analysis, genetic drug development, and consumer genetic testing, among various others. While most current sequencing methods involve chemically altering, amplifying, and labeling the DNA, certain applications in personalized medicine and single cell sequencing require label-free and real-time sequencing that can retain the original DNA sample and accomplish faster turnaround times within the span of a few hours.

Nanopore sequencing is one current technology, and the only currently well-known method that is label-free and well-studied in the field of DNA sequencing. A DNA or RNA sample is passed through an electric field in solution and is directed into either a biological or solid-state nanopore embedded in a membrane substrate. Real-time changes in the ionic current running through the membrane are caused when DNA bases translocate through the nanopore as a result of the electric field and are measured by a sensitive current-measuring detector. Nanopore sequencing has allowed real-time sequencing without the need to label DNA and has now even advanced to 1-2 Mb read lengths in one run.

While this method exhibits capability for reasonably long-read DNA sequencing, problems are present that deter its efficiency and ability to make personalized medicine, as well as other awaited applications an established reality. First, while commercially available devices can provide speeds up to 250 bases/s, the speed is not suitable for personalized medicine applications, where a multitude of genomes must be sequenced much more rapidly. Secondly, a sub-99% base accuracy is reasonable for many applications but is not sufficient for haplotyping and personalized medicine. Thus, much progress still needs to be made in this technology for some of the most essential genomic sequencing applications to become commonplace.

This invention presents an alternate setup and method to detect measurable changes in light and/or ionic current due to base translocation via a nanopore within a novel nanostructure made of graphene that can make sequencing much faster, more accurate, as well as high-throughput. Graphene is attractive as a nanopore substrate material due to graphene's ability to form atomically thin pores and different structures. Main configurations of graphene nanostructures used in the field of sequencing include graphene nanopores, sheets, nanotubes, and nanogaps. Recently, a new shape has been described in a study by Kim et al regarding a "crinkle ruga" structure, which is when graphene buckles over rectangular grooves to form a valley (Kim, K-S et al). Crinkle ruga structures have a flexoelectric effect, or an electromechanical coupling of polarization and strain gradient. As demonstrated with a silica or silicon substrate, graphene buckles inward when strain is applied, which creates a gradient of negative or positive charges, respectively, accumulating at the crinkle valley, a polarization density effect of the flexoelectric effect. The type of charge accumulated depends on the material with the grooves, as Van Der Waals forces present at the edges of the grooves in the material will directly contribute to the flexoelectric coupling effect of the graphene with the material. Control of the structure properties and localization with the substrate choice and radius of curvature used to buckle the graphene is additionally described. Kim et al further studied molecular effects, such as observations of linearizing strands of DNA, at the crinkle, which points to the possibility of using graphene crinkles to study and control location of polar molecules. This is one of the many benefits of graphene in the study of many biomolecules in the field.

For DNA sequencing, graphene has been shown to be capable of ultrafast sequencing, evident in a NIST study where translocation may permit speeds of up to 66 million bases per second (Smolyanitsky, et al.). Due to these speeds, methods to control DNA translocation are required for electrical detection, requiring a specific electrolyte solution which can add to complications while successfully slowing down DNA translocation, such as adding more noise to signal measurement. Additionally, another feature that hinders the effectiveness of current nanopore sequencing is that the orientation of nucleobases within the pore impacts the ionic current signal, thus being one reason for the <99% accuracy rate of this method. Nanopore sequencing probes the structural property of nucleobases and depends on the structural characteristics to create an electronic fingerprint in the current signal, which leads to signal overlapping between structurally similar guanines and adenines, as evidenced in (Derrington et al, 2010). Nanopore sequencing can be improved if it can incorporate an alternative method of physical measurement in addition to the electronic measurements, as well as a way to distinguish each base using other features, such as molecular interactions, in addition to just sampling base dimensions.

An emerging field in biotechnology applications is Localized Surface Plasmon Resonance (LSPR). See, e.g. WO 2016/023010 A1, published Feb. 11, 2016, (Rothberg, Quantum SI) Due to the speed of its optical measurements with label free molecules, easily implementable set-ups, and ease of integration with low power and cost-effective optical components, LSPR is an attractive technology. LSPR is based on the interaction between electron oscillations in the surface of metal nanoparticles and the electric field of incident light. Such nanoparticles can be fabricated from gold, silver, or other coinage metals.

In LSPR, at a resonant wavelength, a localized surface plasmon polariton is excited at the nanoparticle surface, with its frequency highly dependent on the size, geometry, distance between the nanoparticles, and the surrounding medium refractive index. The localized surface plasmon field is highly sensitive to changes in refractive index of the local environment, which can be the result of, but not limited to, interactions with biomolecules near or on the nanoparticle surface. These changes in refractive index can be conveyed as shifts in the resonant wavelength as well as frequency of the reflected or transmitted light.

Nanoparticles used in these applications are commonly of noble metal composition, such as Au or Ag, for their ability to excite LSPR in the visible light range (Krull et al).

Additionally, the geometry of nanoparticles plays a large role in enhancing the electric field between two nanoparticles where LSPR occurs. Geometries including rods or triangles significantly enhance the localized plasmon field between the edges of two very close nanoparticles, which is known as a hotspot. This effect is more pronounced when a triangular nanoparticle dimer is arranged tip-to-tip, also known as a bowtie nanoantenna, is used; the tips of the two triangular nanoparticles can tightly confine the hotspot optical field, thereby enhancing it at values demonstrated to be larger than 10 to the second power for gap spaces smaller than 20 nanometers. This effect occurs with incident light that is polarized and whose electric field is parallel to the major axis of the bowtie configuration. The incident light creating a highly confined electric field within the gap region of the plasmon antenna in between the tips of the triangular nanoparticles positioned in a bowtie configuration. The result of this effect is a gap region with an enhanced sensitivity to small changes in the surrounding refractive index and thereby allowing for the detection of a single molecule or molecular fragment without fluorophores or labels, such as a nucleotide base in a DNA molecule, within the local environment of the confined field within the plasmon antenna. Such measurements can be drastically enhanced with the effect of molecular interactions causing a significant refractive index change in the local environment of the plasmons, adding to the possibility of further resolution than currently achieved with sequencing methods.

By applying an external voltage, molecules with sizes slightly smaller than the pore size are passed through the pore from an electrostatic potential. The nanometer-sized pores are usually embedded in a biological membrane, normally protein nanopores, which exhibit numerous problems with the control of translocation as well as accuracy (Feng et al). They are also formed in solid-state films, such as silicon or graphene, which separates two reservoirs containing conductive electrolytes into cis and trans compartments. Electrodes immersed within each chamber generate fields and help detect electronic signals. Under a biased voltage, electrolyte ions in solution are moved through the pore electrophoretically, thereby generating an ionic current signal. When the pore is blocked by an analyte, such as a negatively charged DNA molecule added to a cis chamber, current flowing through the nanopore would be blocked, interrupting the current signal (Feng et al). The physical and chemical properties of the target molecules can be calculated by statistically analyzing the amplitude and duration of transient current blockades from translocation events (Venkatesan et al). Solid-state nanopores have many advantages over biological nanopores, including more stability. Graphene nanopores, in particular, exhibit an extraordinarily high potential for DNA sequencing, showing increased spatial resolution.

The fast translocation of DNA bases presents an issue with current sequencing using nanopores (Liu et al). Nucleotides provide unique electronic signatures with regards to orientation in the pore and charge properties (Feng et al). Controlling the position of the nucleotides within the nanopore will be instrumental to improving nanopore sequencing accuracy and utility.

This invention addresses the ongoing need for fast, inexpensive, and high-throughput nanopore devices for molecular detection that can be used in the field to sequence real-time and label-free nucleic acid samples. Quick and inexpensive yet accurate DNA sequencing is an ongoing challenge. The field of personalized medicine can be greatly benefitted with a device that allows for real-time sequencing compatible with droplet-based methods of transferring DNA, which can lead to rapid sequencing of many genomes in a shorter span of time, which is especially required for fields regarding newborn health analysis and pandemic crises. Nanopores of current devices still require specific electrolyte solutions and environments of the DNA, which hinders progress in this area and slows transition of nanopore sequencing into some fields. What is needed in view of these existing technologies is a technology that improves on current nanopores by providing for the direct and diverse measurements of shifts in light intensity and frequency in addition to electronic signals alone, in order to match the translocation speeds of nucleobases in the pore. Necessary as well are nanopores that have higher capabilities of sensing by probing the molecular characteristics in conjunction with the interactive behavior of each nucleobase for better discrimination, and directly controlling molecular orientation within the nanopore for reproducible results with varied quality of the medium used. Such methods can flexibly work with a variety of solutions and methods for different needs and purposes across industry and research pursuits.

SUMMARY OF THE INVENTION

In an embodiment, this invention provides a chip for sequencing a strand of nucleic acids. In an embodiment, the chip includes a substrate fabricated from silicon or silica about 1.0 μm to about 10 μm wide, about 1.0 μm to about 10 μm long, with a thickness of about 500 nm to 2.0 μm. The substrate may have a central groove about 100-500 nm wide and about 30-300 nm deep etched into the top surface of the substrate. A multilayer graphene sheet about 1-60 nm thick is affixed to the substrate in a latitudinal orientation, with a pair of electrodes on each end of the graphene sheet (also referred to herein as a ribbon) and wherein the graphene sheet is subjected to lateral compression to cause a p-type crinkle ruga having a central crease to form thereon over the central groove. The graphene sheet further includes one or more nanopores of about 0.3 to 3.0 nm wide at the center line of the crinkle ruga crease. In an embodiment a patch clamp amplifier measures changes in an ionic current passing through the nanopore. The ionic current can be used to assign specific nucleobases (A, T (U), C, G) passing through the nanopore. In an embodiment, the chip further comprises a base substrate layer of silicon nitride, alumina, or boron nitride.

Also disclosed is a method of detecting and assigning nucleobases in a strand of nucleic acids, comprising a chip with a graphene sheet as described above, and directing a saline solution of the nucleic acid comprising a strand of nucleobases toward a nanopore in the graphene sheet, wherein the nucleobase strand translocates through the pore and interacts with the layers of the multilayer graphene sheet, and the patch clamp amplifier measures changes in the ionic current and detects each nucleobases in the nucleic acid strand translocating through the nanopore and the nucleic acid sequence is assigned.

In another embodiment, a chip for sequencing a strand of nucleic acids is provided. The chip is a substrate fabricated from silicon or silica about 1.0 μm to about 10 μm wide, about 1.0 μm to about 10 μm long, with a thickness of about 500 nm to 2.0 μm. Each substrate may have a central groove about 100-500 nm wide and about 30-300 nm deep etched into the top surface of the substrate. A multilayer graphene sheet 1-60 nm thick may be affixed to the substrate in a latitudinal orientation, with a pair of electrodes on each end of the graphene sheet. The graphene sheet may be subjected to lateral compression to cause a p-type crinkle ruga having a crease to form thereon longitudinally over the central groove. The graphene sheet may include one or more nanopores of about 0.3 to 3.0 nm width at the center line of the sheet according to a longitudinal axis of the chip. In an embodiment, the substrate has one or more light apertures extending from the bottom of the central groove to the lower surface of the chip, and wherein each nanopore is aligned with a light aperture. A layer of an optically transparent material such as PDMS, plastic, or SiO2 is deposited on the lower surface of the central groove, and a plasmon antenna is provided on the bottom surface of the central groove, aligned longitudinally with the chip, and a laser light source is provided the directs a light beam through the aperture, and wherein a photodetector is provided above the graphene sheet or ribbon.

In an embodiment, a method is provided for detecting nucleobases in a strand of nucleic acids, comprising a chip with a graphene sheet as described above, and directing a saline solution of the nucleic acid strand toward a nanopore in in the graphene sheet, wherein the nucleic acid strand translocates through the pore and interacts with a plasmonic resonance cell excited by an appropriate light source and alters the plasmonic resonance of the cell. A photodetector can detect variations in the refracted light from the plasmonic resonance, and the nucleobase can be assigned according the characteristics of the refracted light from the plasmonic cell.

In an embodiment, a method is provided for detecting and assigning nucleobases in a strand of nucleic acids, comprising a chip with a graphene sheet as described above, and directing a saline solution of the nucleic acid strand toward a nanopore in the graphene sheet, wherein a positive electrical potential from the flexoelectric effect of the crinkle ruga on the graphene sheet interacts with polar nucleobase groups to force the nucleic acid strand to align with the nanopore and to translocate through the pore. An appropriate light source causes plasmon resonance between the plasmon antennae. The strand of nucleic acid translocating through the pore in the sheet alters the plasmon resonance, and the photodetector can detect variations in the refracted light from the plasmon resonance, and the nucleobase can be assigned according the characteristics of the refracted light from the plasmonic resonance.

In an embodiment, a chip for sequencing a strand of nucleic acids is provided, wherein the chip includes a substrate fabricated from silicon or silica about 1.0 μm to about 10 μm wide, about 1.0 μm to about 10 μm long, with a thickness of about 500 nm to 2.0 μm. Each substrate has a central groove about 100-500 nm wide and about 30-300 nm deep etched into the top surface of the substrate. In an embodiment, a multilayer graphene sheet 1-60 nm thick is affixed to the substrate in a latitudinal orientation, and a pair of electrodes is connected to each end of the graphene sheet and wherein the graphene sheet is subjected to lateral compression to cause a crinkle ruga to form thereon over the central groove. In an embodiment, the graphene sheet has a layer of gold or other coinage metal 1-40 nm thick deposited thereon, and the graphene sheet has one or more nanopores about 0.3 to 3 nm wide at the center line of the sheet according to a longitudinal axis of the chip. The substrate may have one or more light apertures extending from the bottom of the central groove to the lower surface of the chip, and each nanopore may be aligned with a light aperture. A layer of an optically transparent material such as PDMS, plastic, or $SiO_2$ may be deposited on the lower surface of the central groove, and a laser light source may be provided that directs a light beam through the aperture, and wherein a photodetector is provided above the graphene sheet or ribbon.

In an embodiment, an array for sequencing the nucleobases that comprise a strand of nucleic acids is provided. The array may be a set of wells 300 to 500 nm wide fabricated in a silicon substrate 100 to 500 μm thick and optionally having a base substrate layer of silicon nitride, alumina, or boron nitride. A channel 200 to 500 nm wide may be drilled into each well through the silicon substrate and base layer to form a microfluidic exit for a DNA sample. A multilayer graphene sheet 1-60 nm thick may be affixed to the substrate, with an electrode on each side of the graphene sheet, and the graphene sheet may be subjected to lateral compression to cause a P-type crinkle ruga crease to form thereon over each well. One or more pores about 0.3 to 3.0 nm wide may be drilled into the crease of the graphene sheet over each microfluidic channel. An electrical potential may be applied across the graphene sheet through the electrodes, and wherein a DNA sample is translocated through the pores in the graphene sheet and directed into the microfluidic exit channels.

DETAILED DESCRIPTION

Figure 1:
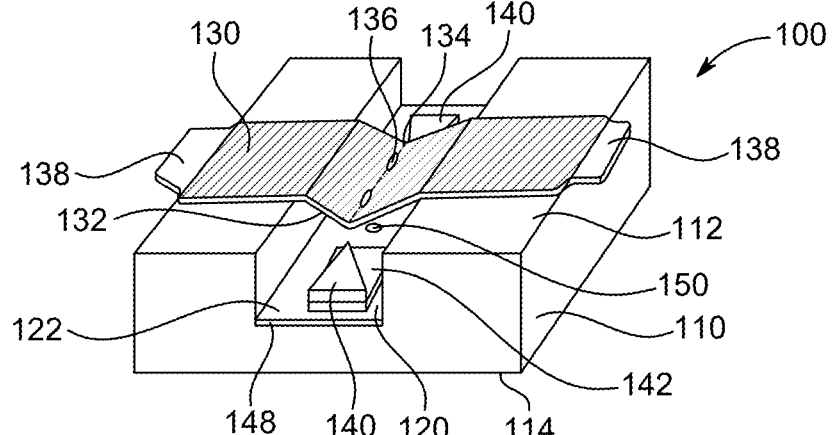
FIG. 1 is a perspective view of the inventive chip.
Figure 2:
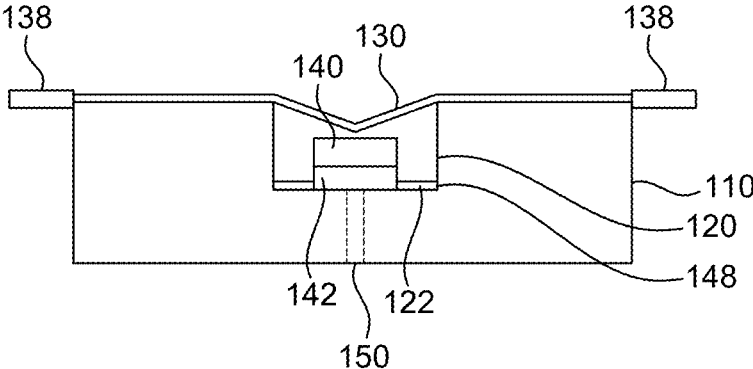
FIG. 2 is a front elevation view of the inventive chip.
Figure 3:
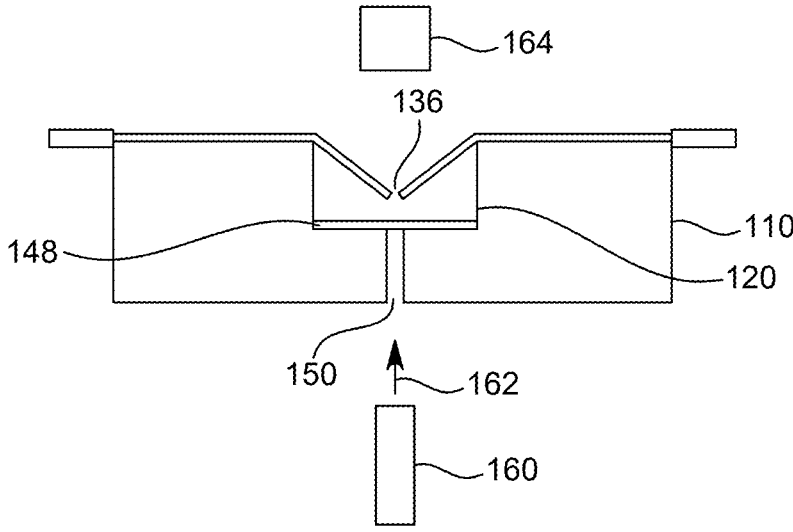
FIG. 3 is a latitudinal cross section of the inventive chip and includes generic depictions of a laser light source and a photodetector.
Figure 4:
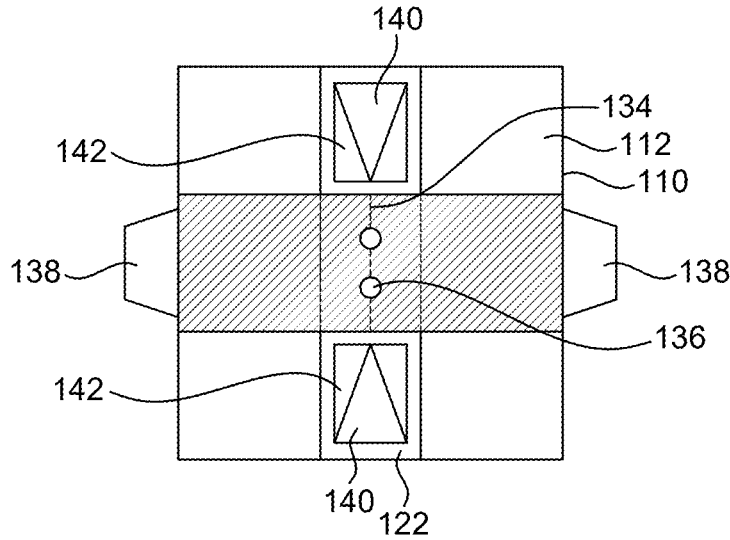
FIG. 4 is a top view of the inventive chip.

Disclosed herein is a nano-sensing device capable of very high throughput nucleic acid sequencing, in which a polarized graphene sheet or sheet forces a nucleic acid strand to translocate through a nanopore in the graphene, and align proximal to a plasmon resonance cell. Detection of the nucleobases that comprise the nucleic strand as they translocate through the graphene can be accomplished by several methods. In an embodiment, localized surface plasmonic resonance (LSPR) may be used, employing a suitable light source directed at the cell and coupled to an appropriate detector can distinguish various nucleic acid bases as they pass over the plasmonic cell according to changes in the refractive index of the light beam caused by LSPR. In another embodiment, ionic currents can be used with an ionic current detector that can determine electrical "signatures" of specific nucleobases as they translocate through a nanopore in a graphene sheet, and assign the nucleobases (A, C, T, G) based on the electrical characteristics. The nucleic acid strand may be comprised of nucleotides or nucleosides, and may be from a natural source, such as isolated from a cell, such as a bacteria, plant or animal cell, or extracted from a viral source. A nucleic acid strand may be comprised of deoxynucleic acid (DNA) or ribonucleic acid (RNA).

This invention discloses a high-throughput single cell sequencing device capable of label-free sequencing that does not require chemical modifications or cell cultures of individual cells to be analyzed. The disclosed DNA sequencing instrument would be capable of massive parallel and label-free sequencing that can be completed faster (under 2 hours) and cheaper than conventional technologies for single cell nucleic acid sequencing applications in the pharmaceutical industry, biotech R&D, and healthcare. Our platform utilizes an improved nanopore sequencing technology, using unique graphene nanopores with optical or electrical properties that can detect and distinguish nucleic acid bases in a nucleic acid strand. We have demonstrated interactions with DNA as proof-of-concept data for label-free and cost-effective sequencing. We would be able to integrate droplet transport of DNA fragments into our sequencer to directly read nucleotides via electrical or optical interactions in order to make single cell sequencing faster, high-throughput, and cost-effective for personalized medicine and applications in genetics and immunotherapy advancement.

As used herein, the term "about" implies a dimension that is not critically precise, and the term "about" implies ±20% of the stated value.

Nanopore Bio-Sensing Device

Accordingly, as shown in FIGS. 1-4, the present application discloses an embodiment of a high-throughput nanopore bio-sensing device 100, comprising a grooved silicon or silica (PDMS/SiO$_2$) substrate 110, a V-shaped graphene nanostructure comprising a sheet or ribbon 130 with at least two layers of graphene, at least one nanopore 136 within the localized point of the V-shaped graphene nanostructure where the graphene is bent (134), two electrodes 138 positioned at the ends of the graphene nanostructure, an opening 150 at the bottom of the groove 122 within the substrate for light to enter and excite the nanostructure, a collection nano/microfluidic channel situated above or proximal to the light opening at the bottom of each groove that can carry the original biomolecule samples away from the plasmon cell.

Figure 5:
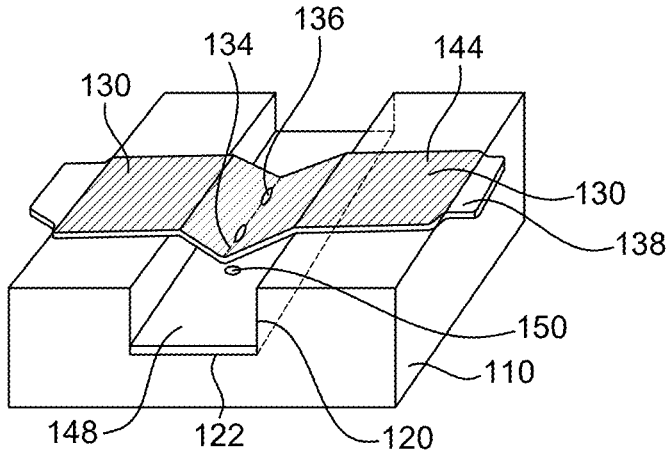
FIG. 5 is a perspective of an alternative embodiment with gold or other coinage metal deposited on the multilayer graphene sheet.
Figure 6:
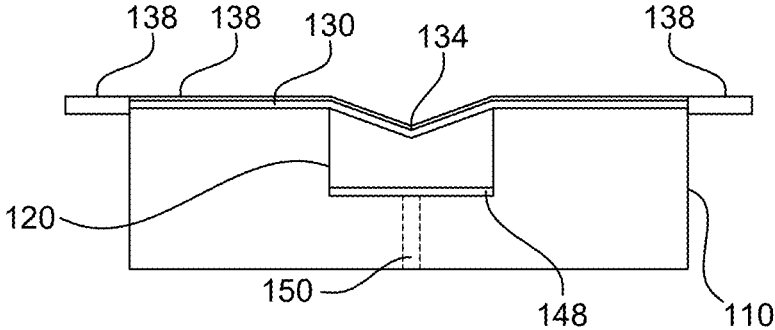
FIG. 6 is a front elevation view of the alternative embodiment with gold or other coinage metal deposited on the multilayer graphene sheet.
Figure 7:
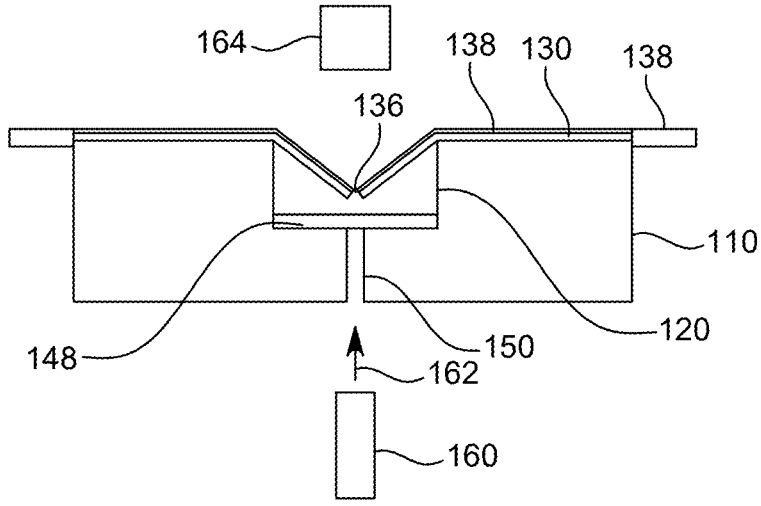
FIG. 7 is a latitudinal cross section of the alternative embodiment with gold or other coinage metal deposited on the multilayer graphene sheet and includes generic depictions of a laser light source and a photodetector.

In shown in FIGS. 5 and 6, the present application discloses an embodiment of a high-throughput nanopore bio-sensing device 100, comprising a grooved silicon or silica (PDMS/SiO$_2$) substrate 110, a V-shaped graphene nanostructure comprising a sheet 130 with at least two layers of graphene, at least one nanopore 136 within the localized point of the V-shaped graphene nanostructure where the graphene is bent (134), two electrodes 138 positioned at the ends of the graphene nanostructure, an opening 150 at the bottom of the groove 122 within the substrate for light to enter and excite the nanostructure, a collection nano/microfluidic channel situated above or proximal to the light opening at the bottom of each groove that can carry the original biomolecule samples away from the plasmon cell.

The chips as described in FIGS. 1-7 may additionally include a base substrate layer 116 of silicon nitride, Si$_3$N$_4$, aluminum oxide (Al$_2$O$_3$), or boron nitride (BN). These materials, including silicon dioxide (silica, SiO$_2$) films have been widely used as substrates because of their low mechanical stress and high chemical stability (Feng et al. 2015). Solid-state nanopores have many superior advantages over their biological counterparts, such as chemical, thermal, and mechanical stability, size adjustability, and integration. Additionally, these films can operate under a wide range of experimental conditions and can be mass produced using conventional semiconductor processes. If present, a base layer of Si$_3$N$_4$, Al$_2$O$_3$, or BN is shown in FIGS. 8-10 as 116.

The microfluidic channels 150/152 may be drilled as round (150) or square or rectangular (152) holes in the silicon 110 and base substrate layer 116 (if used) substrates.

In an embodiment, the instant invention may improve measurements by using the positive charge within the graphene crinkle as a way to electronically probe and electrostatically position each nucleotide within the pore. The positive charge attraction to the negatively charged DNA molecule will also slow down the translocation, providing a means to control translocation while potentially simplifying measurement of ionic current in 0.3-1M KCl solution to single base resolution using charges within the graphene to 1) position nucleotides within the pore with more reliable orientation within the pore, while also 2) forming temporary electrostatic interactions with nucleotides for enhanced single base resolution, and 3) analyzing charge characteristics of specific nucleobases. Measurements of ionic current can be efficiently conducted under 120-180 mV potentials across the membrane with detection equipment such as a patch clamp amplifier, for example, an Axon™ Axopatch™ 200B. The electric signatures as ionic current fluctuations occur during DNA translocation through the nanopore and caused by blockages within the nanopore (Deamer, 2002) will be converted to nucleotide-specific reads by circuitry that records information from the amplifier or patch equipment. Fluctuations of the ionic current will reflect charge in the graphene crinkle at the single-base level in a millisecond time scale directly correlating to nanoscale electronic interactions between the polarization within the graphene layers and the nucleotides. Information will be obtained and converted into base assignments as a readable format via specialized software that utilizes algorithms for translation of known electronic signatures within ionic current measurements taken during sequencing runs. The potential for less noise and increased signal quality is evident, as the positive charge within the graphene crinkle will slow down translocation and potentially improve signal quality, thereby removing the need for increased electrolyte solution to slow down DNA translocation in conventional nanopore methods (Wang, 2015). Compatibility for droplet delivery methods are also implied, since the natural curvature of the crinkle as well as charge polarization will work together to draw DNA into the nanopore without need for delicate enzymes or complex microfluidic processes. Such a benefit would add multiplexed, real-time single cell sequencing technologies to the field that also preserve sample quality and directly analyze physical, structural, and epigenomic properties of DNA via electronic probing, which contribute a new layer of data to single cell analyses per run with drastically reduced chemical preparation in shorter timeframe.

Figure 8:
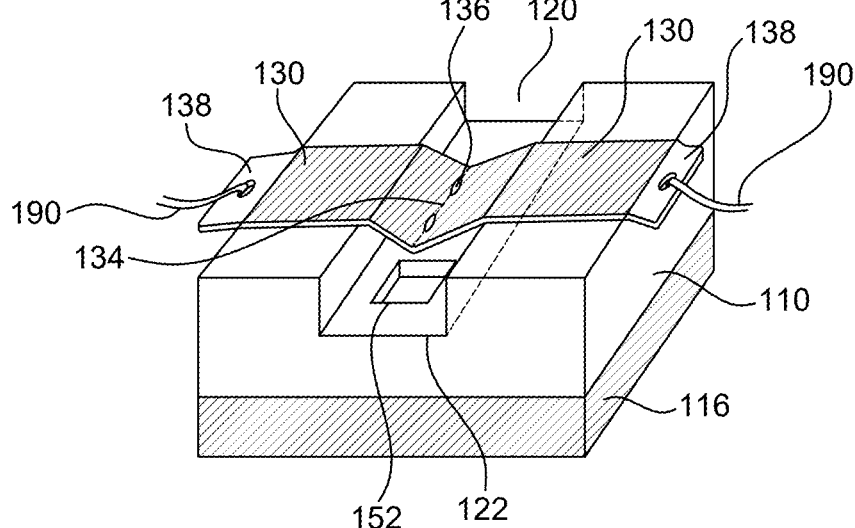
FIG. 8 is a perspective view of a chip with a $Si_3N_4, Al_2O_3$, or BN, useful as a substrate for a microfluidic exit channel.
Figure 9:
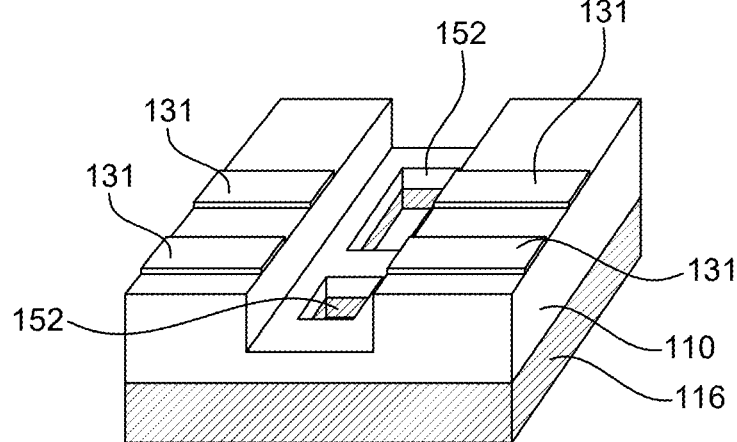
FIG. 9 is an alternative view of the same device as FIG. 8, with the graphene sheet (or ribbon) cut away to show the microfluidic exit in the groove of the chip for electrophoretic translocation.
Figure 10:
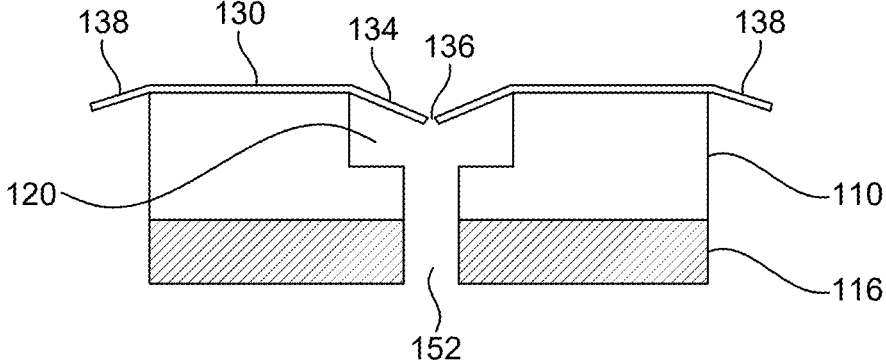
FIG. 10 is a cross section through a device as depicted in FIG. 8, showing the microfluidic channel.

In FIGS. 8-12, electrodes 138 (example: Ag/AgCl electrodes) on the graphene layers are connected to an ionic current detector (for example, a patch claim amplifier) with leads 190. Holes may be drilled through the floor of the groove 120 that holds the crinkle ruga. In this embodiment, a base layer of silicon nitride, alumina, or boron nitride (116) holds the silicon chip as a channel to lead the DNA out of the silicon and capture the DNA samples. A medium such as water may flow through the graphene and through the hole in the floor of the groove 120 leading to the base layer channel 152 so that DNA can flow and electrophoretically translocate through the pore and out of the channel. FIG. 9 is the same perspective as FIG. 8 but with the graphene layers cutaway to show the arrangement of channels 152 in the floor of groove 120. FIG. 10 is a cross section of the device of FIG. 8, showing graphene sheet (or ribbon) 130, crease 134, pore 136 in the graphene sheet, groove (well) 120, and channel 152, forming a microfluidic channel for electrophoretic translocation.

Figure 11:
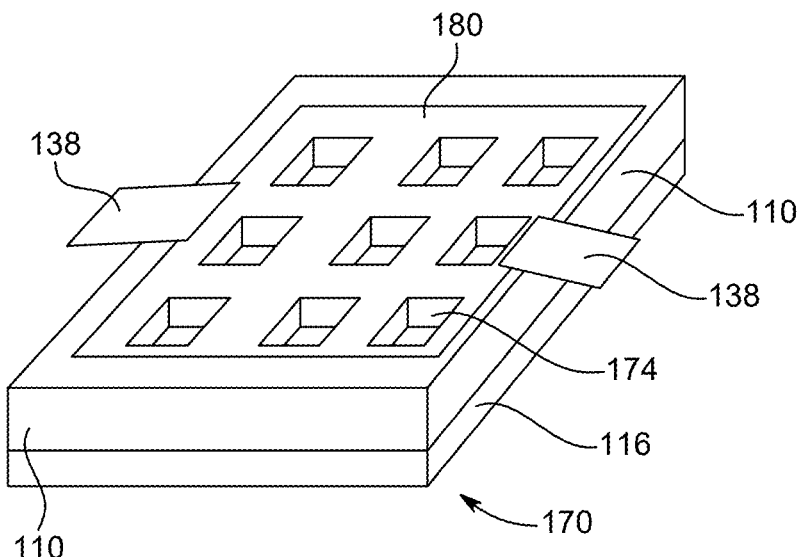
FIG. 11 is a 3×3 microarray showing nine wells in a square or rectangular chip.
Figure 12:
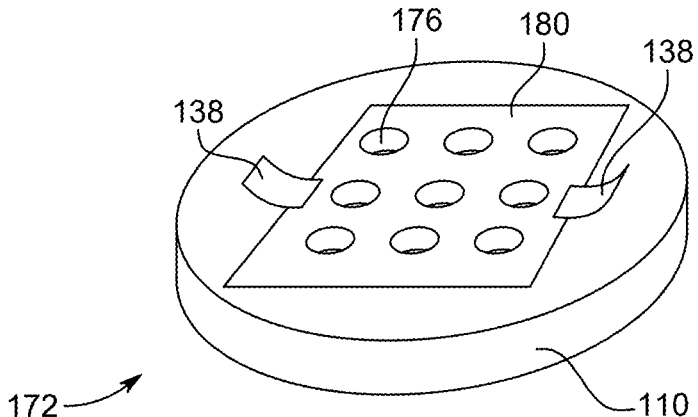
FIG. 12 is a 3×3 round microarray.

FIGS. 11 and 12 show a detector array embodiment. FIG. 11 is a square embodiment and 3×3 array, with square wells 174. Each well is equivalent to a discrete chip with a groove such as depicted in FIG. 1-10. In FIG. 11, a silicon chip 3 mm wide and 0.2-0.5 mm thick is shown, optionally with a base later 116. Wells can be drilled as square holes of 500 nm width. The holes will be drilled through the silicon layer 110 and also through the base layer if present to form a microfluidic channel (152). In an alternative embodiment, the array may be prepared as a circular device 172 in FIG. 12. Wells can also be circular (176) as depicted in FIG. 12, which might be easier for multiplexed E-beam drilling. The array of wells 172 or 174 is pictured, adding visual of multiplexing capabilities for the chip. This array is not limited to a 3×3 array, and can be any size, such as for example 10×10, 100×100, 1000×1000 or any size in between. In an alternative embodiment, rather than an array of wells, grooves can be etched or otherwise drilled in rows on a chip. Microfluidic channels 150 or 152 would be placed in the grooves The graphene is placed as a sheet over surface of silicon chip 110 depicted in FIG. 11 or 12. The graphene may be a sheet of multilayer graphene (MLG), that may be 2-7 sheets (or more) of graphene, placed over the chip surface. The graphene will naturally adhere to the silicon surface. Pressure may be applied to cause the crinkle ruga graphene buckling into each hole. TEM may be used to drill the required nanopores in the graphene creases.

Figure 13:
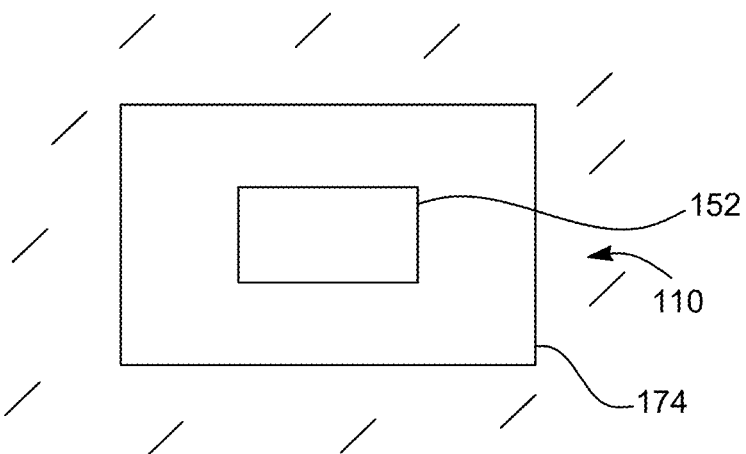
FIG. 13 is an elevation view of a well in the microarray showing the microfluidic channel in the floor of the well.

FIG. 13 is a detail overhead view of a square well 174 drilled in silicon chip 110 with microfluidic channel 152 in the center. The channel 152 may be drilled inside of the 100 nm deep groove, so the channel will be between 200 and 500 nm wide (if it is 500 nm, then this hole becomes essentially a channel through the entire silicon structure, with the graphene buckled over this channel). FIG. 10 shows the channel 152 being nearly the entire width of groove or well 120, forming an almost full width channel through the entire silicon chip 110 and base layer 116 if present.

In an embodiment, the MLG sits over the wells or grooves 120 in the silicon layer 110 and can sit over a base layer 116 that can have microfluidic capabilities to capture and transport DNA with beads. The benefit of this design and that in FIG. 10 is that droplets can transport DNA, efficiently speeding up the single cell sequencing process, and be pulled into the graphene crinkle crease within the Si by attracting DNA easily with the positive charge located in the crease. The crinkle also physically draws the droplet into the crease, making nanopore transition and making translocation much easier, combined with the positive charge in the graphene layers. Current nanopore technologies using conventional flat substrates (for example, Rang 2018) cannot incorporate droplets due to having to aim a large droplet perfectly over a sub 2-nm pore and reliably lead DNA to the nanopore once in solution. The inventive design allows droplets to be captured in a structure first, then positive charges pull and align DNA into the nanopore, allowing easier translocation into the nanopore that is 2 nm wide or less. Integrated microfluidic systems can flush the nanopore with electrolyte solution to allow electrophoretic translocation.

The graphene nanostructure 130 with nanopore(s) may be further inclusive of a plasmonic resonance cell, comprising two antennae 140 in the shape of rods, triangles, spheres, or any shapes that are capable of exciting a localized optical hotspot in a gap between the two antennae (FIGS. 1-4). Substrate layers of Si, $SiO_2$, or glass may be deposited within the Si grooves of the Si grooved substrate, where gold, silver, or any other coinage metal may be deposited onto and fabricated into localized surface plasmon antenna nanostructures. The two plasmonic nanostructures 140 are positioned tip to tip or end to end to create a hotspot between the gap. This gap will ideally be 20 nm or less between the plasmon antennae. Their location will be proximal to the crease (also termed the "crinkle") of the bottom of the V-shaped graphene nanostructure, where the nanopore will be located. In an embodiment, platforms 142 may be provided to elevate the plasmon antennae to a position very close to a nanopore 136 in the graphene sheet. By elevating the antennae 140 to a position closer to the nanopores 136, the alignment of a nucleic acid strand translocating through a nanopore 136 will be more precise, resulting in a stronger, lower noise surface plasmon effect that is used to assign the nucleic acid bases in the strand.

In an embodiment, light is transmitted upward via a laser or diode source 160 and is transmitted through aperture 150 at the bottom the groove within the Si substrate. The light will interact with biomolecule in the plasmonic cell and excite the plasmonic nanostructures. Light will be collected upward above the structure by photodetector 164 as it transmits through the nanopore in the graphene nanostructure, collecting information about translocating biomolecules as either shifts in the refractive index, resonant wavelength, frequency, or light intensity. The inverse of the measuring system, inverting the positions of light source 160 and photodetector 164, may also be possible in an alternative embodiment. In this alternative embodiment, the light source will be positioned above the graphene sheet or ribbon and transmitted downward through the nanopore 136 and through aperture 150 to a detector below the chip.

In an embodiment, a nano/microfluidic channel may be provided within the grooves of the Si substrate and over the light entry opening. The nano/microfluidic channel in this embodiment can be fabricated with a layer of an optically transparent material such as polydimethyl siloxane (PDMS), plastic, or $SiO_2$ (148). Aqueous solutions can flow through the channel via an inlet or opening structure where the grooves begin at either end of the substrate. The aqueous solutions can be directed out of the grooved nano/micro fluidic channel into an exit channel or opening, for the purpose of collecting the original biomolecule sample. A pump can be included.

Sensing of biomolecules will be designed to have molecules such as nucleobases (DNA or RNA molecules) interact with the layers of graphene in the nanopore. Due to the positive charge localization at the valley of the crinkle ruga, bases will interact with the charges effected from each layer as it translocated through the multi-layer nanopore. Problems solved with this design include: 1) Interaction based measurement will lead to a higher refractive index change in the plasmonic structures, leading to possible single base detection and decreasing chances of missing bases during detection. 2) Multiple layers of graphene and sensing done at multiple layers will remove noise by adding different points of measurement, as well as measuring further down in the layers, since vibrations from DNA or other molecules entering the nanopore at beginning layers add to noise, such as in single substrate nanopore sequencing. 3) A high electrolyte solution will not be required to slow down DNA translocation, since optical measurements are much faster, so this technology can be integrated with various methods. 4) The method can be multiplexed and achieve a high throughput with simple optical set-up. 5) This nanopore set-up can be capable of using beads to help initiate DNA translocation, as interaction-based measurements can allow the bead not to interfere with measurement design.

Dimensions

A semiconductor chip (substrate unit) 100 of this invention may be about 1.0 μm to about 10 μm wide, and its length can be about 1.0 μm to about 10 μm, with a thickness of about 500 nm to 2.0 μm. The width of the central groove 120 etched in the substrate may be about 100-500 nm. In an embodiment, the depth of grooves 120 is 30-300 nm. The length of grooves can span up to the length of Si substrate, if necessary, but can also be less for integration into a nano/micro fluidic channel within the Si chip.

Graphene Nanostructure

Each chip may have a multilayer graphene (MLG) sheet or sheet 130 having graphene layers that may have a total thickness (all layers) of from about 1 to 60 nm thick, although in most embodiments, a total thickness towards the lower end of this range, up to about 5 nm thick may be more desirable for efficient translocation of nucleic acid molecules. Kim 2018 provides a guide for tailoring graphene layers and groove lengths for graphene nanostructure to be ideal for applications. Typically, these sheets are tens to hundreds of layers of graphene. Electrodes can be placed on the ends of the strip of the multi-layer graphene to create an electric field. Nanopores 136 within the graphene nanostructure may be about 0.3 to 3.0 nm in width. A layer can be placed over the top-most graphene surface of dielectric material (SiO$_2$, Al$_2$O$_3$) for passivation of the graphene to minimize surface sticking events without impacting inner layer measurements.

In an embodiment, the graphene sheet or ribbon 130 is draped over the central groove 120 and configured with sufficient lateral compression to form a "P-type" crinkle ruga (Kim 2018), with a downward crease over the gap of the central groove. The nanopores 136 are fabricated in the center of the graphene sheet over a center line of the central groove 120, shown in FIG. 4. A P-type crinkle ruga will have a positive electrostatic charge from the flexoelectric effect of the crinkle ruga.

Plasmonic Nanostructures

In an embodiment, detection of nucleobases may employ plasmonic nanostructures. Plasmonic nanostructures 140 are a pair of metallic nanoparticles, typically gold or silver, in the shape of rods, triangles, spheres, or any shapes that are capable of exciting a localized optical hotspot in a gap between the two nanoparticles (also termed antennae). The nanostructures can be 15-50 nm thick. Length may vary, at least 20 nm for rods, and triangle side lengths can also be at least 20 nm long. The gap between structures can be 20 nm or less. A structure may also be a sharp end-rod, any structure capable of localized surface plasmon resonance is usable, as long as the gap region remains 20 nm or less. A Ti/Cr layer must sit between the substrate and the metal nanoparticles to provide adhesion, and should be up to 5 nm, but ideally as small as possible.

In an embodiment, the plasmonic nanostructures 140 may be on elevated structures 142 that assist in positioning the nanostructures 140 in close proximity to a nanopore 136 in the graphene ribbon.

In an embodiment (FIGS. 5-7), there may be no discrete plasmonic nanostructures 140 or elevated parts 142. Rather, a layer of gold (138), or any coinage metal capable of exciting plasmon resonance can be deposited over the graphene sheet 130, with a thickness of about 1 nm to 40 nm. In an embodiment, the gold or other metal is not thicker than the graphene, and preferably is a somewhat thinner layer. For example, the graphene sheet may be about 5 nm thick (all layers of the multilayer graphene), and the gold deposited may be about 3 nm thick. A nanopore 136 (same dimensions as described) can be drilled with TEM into the layer and through the graphene 130/138. An oxide layer (SiO$_2$, Al$_2$O$_3$) can be placed over the gold or other coinage metal layer to prevent sticking of the DNA to the gold prior to drilling the nanopore through the layers. The sensing method would be the same in this embodiment. There would be no need to fabricate platforms then with this method. In this method, the plasmonic effect would be caused by metal integral with the graphene sheet, rather than discrete plasmonic antennae.

Nano/Micro Fluidic Channel

A nano/micro fluidic channel may be provided at the bottom of the groove and between the substrates holding the nanostructures will capture the DNA, and can flow the width of the chip, away from the grooves, as shown in figure. The nano/micro fluidic channel may be made of optically transparent material, such as polydimethyl siloxane (PDMS), plastic, or an such as SiO$_2$ or Al$_2$O$_3$. Water will flow over the channel made, leading to a chamber, outlet, where sample can be collected with or without binding resin.

Light Opening

In an embodiment, an aperture 150 is provided spanning the bottom of the substrate to the floor 122 of the central groove. The aperture 150 may be a slit, hole, or any shaped opening at the bottom of the groove will allow light to excite the structures and provide a system for measurement. Excitation light (500 nm-1,200 nm) will also be sampled for output data, as changes in the light provide direct measurement and details about the sample.

Collection of light will be done via any optical detector, such as spectrometer, photodiode, any other device known to someone familiar with the field.

Fabrication

Silicon (Si) substrate grooves can be milled with FIB (focused ion beam) or EBL (electron beam lithography).

Graphene nanostructures 130: multi-layered graphene can be mechanically exfoliated and will naturally adhere to the oxidation layer of the silicon, so it can be layered flatly over the grooved substrate. A nanopore 136 can be created before creating the crinkle ruga with controlled diameter using TEM or other methods known to those in the field. To make the structure form a valley where charges localize and the nanopore is centered, strain must be applied. The magnitude of the peak curvature is varied by both groove geometry and substrate strain (Kim et al). Placing the substrate over a lens of chosen radius and releasing it will cause the multilayered graphene to buckle downward and form a crinkle ruga with a positively charged curvature point. Maximum local compressive strain should be 0.2%. Plasmonic nanostructures 140 can be fabricated with deposition and EBL techniques, as well as the substrates and light opening.

EXAMPLES

Example 1

A process for fabricating the inventive device is as follows
a) Create grooved Si substrate
b) Create light opening at bottom of grooves with EBL, TEM, or any other method
c) Cover bottom with optically transparent material and create an extended channel away from the grooves (shown in figure) for nano/micro fluidic channel creation
d) Layer flat multilayered graphene over the grooved substrate so it adheres naturally (graphene will flatly lay over the grooves)
e) Use a protective resist material (such as PMMA) to protect strip of graphene at desired location and get rid of unnecessary extra graphene with lithography
f) Create nanopore with TEM in the graphene within 50 nm center in the middle
g) Deposit substrates within grooves, separate with EBL to create a gap opening for samples to fall into groove between them, as shown in figure
h) Put e-beam resist at planned location of nanoparticles on substrates
i) Place chip over lens and lightly compress, then release substrate
j) Deposit metal, use lift-off method, obtain plasmon nanostructures
k) Passivate graphene with deposition of oxide layers

Example 2

A process for fabricating the inventive device is as follows:
a) Create grooved Si substrate
b) Create light opening at bottom of grooves with EBL, TEM, or any other method
c) Cover bottom with optically transparent material and create an extended channel away from the grooves (shown in figure) for nano/micro fluidic channel creation
d) Layer flat multilayered graphene over the grooved substrate so it adheres naturally (graphene will flatly lay over the grooves)
e) Use a protective resist material (such as PMMA) to protect strip of graphene at desired location and get rid of unnecessary extra graphene with lithography
f) Place chip over lens and lightly compress, then release substrate
g) Deposition of gold layer, then deposit oxide layer atop gold (oxide layer ideally less than 5 nm) (if wish to passivate graphene, then passivate graphene with deposition of oxide layers prior to depositing layer of gold and its covering oxide layer)

h) Create nanopore with TEM in the graphene within 50 nm center in the middle

BIBLIOGRAPHY

Deamer, D. W., and Branton, D. (2002). Characterization of nucleic acids by nanopore analysis. *Acc. Chem. Res.* 35, 817-825. doi: 10.1021/ar000138m Derrington, I. M., Butler, T. Z., Collins, M. D., Manrao, E., Pavlenok, M., Niederweis, M., et al. (2010). Nanopore DNA sequencing with MspA. *Proc. Natl. Acad. Sci. U.S.A.* 107, 16060-16065. doi: 10.1073/pnas.1001831107

Yanxiao Feng, Yuechuan Zhang, Cuifeng Ying, Deqiang Wang, Chunlei Du., "Nanopore-based Fourth-generation DNA Sequencing Technology," Genomics, Proteomics & Bioinformatics, 2015, 13(1) 4-16; https://doi.org/10.1016/j.gpb.2015.01.009; erratum 2015, 13 (6) 383, https://doi.org/10.1016/j.gpb.2016.01.001

Daniel J Giguere, Alexander T Bahcheli, Benjamin R Joris, Julie M Paulssen, Lisa M Gieg, Martin W Flatley, Gregory B Gloor; Complete and validated genomes from a metagenome, bioRxiv 2020.04.08.032540; doi: https://doi.org/10.1101/2020.04.08.032540

Kim, K-S et al., "A New Subcritical Nanostructure of Graphene—Crinkle-Ruga Structure and Its Novel Properties," MRS Advances, 2018, 3(45-46) (Nanomaterials), 2763-2769, https://doi.org/10.1557/adv.2018.432

S. Liu, Q. Zhao, J. Xu, K. Yan, H. L. Peng, F. H. Yang, et al., "Fast and controllable fabrication of suspended graphene nanopore devices," Nanotechnology 2012, 23(8), 085301. doi: 10.1088/0957-4484/23/8/085301. Epub 2012 Feb. 1.

Rang, F. J., Kloosterman, W. P. & de Ridder, J. From squiggle to basepair: computational approaches for improving nanopore sequencing read accuracy. Genome Biol 19, 90 (2018). https://doi.org/10.1186/s13059-018-1462-9

Smolyanitsky, A. et al. "Nucleobase-functionalized graphene sheets for accurate high-speed DNA sequencing," Nanoscale, 2016, 8, 1861-1867, https://doi.org/10.1039/C5NR07061A B. M. Venkatesan, B. Dorvel, S. Yemenicioglu, N. Watkins, I. Petrov, R. Bashir, "Highly sensitive, mechanically stable nanopore sensors for DNA analysis" Adv. Mater., 2009, 21, 2771-2776. doi:10.1002/adma.200803786

Verschueren D V, Pud S, Shi X, De Angelis L, Kuipers L, Dekker C. "Label-Free Optical Detection of DNA Translocations through Plasmonic Nanopores" *ACS Nano.* 2019 Jan. 22; 13(1):61-70. doi: 10.1021/acsnano.8b06758. Epub 2018 Dec. 4. PubMed PMID: 30512931; PubMed Central PMCID: PMC6344913.

Wang, Yue et al. "The evolution of nanopore sequencing." *Frontiers in genetics vol.* 5 449. 7 Jan. 2015, doi:10.3389/fgene.2014.00449

DRAWINGS LEGEND

| | |
|---|---|
| 100 | Biosensing chip |
| 101 | Biosensing chip-plasmon integral with graphene sheet |
| 110 | substrate |
| 112 | Upper surface of substrate |
| 114 | Lower surface of substrate |
| 116 | Silicon nitride, alumina, or boron nitride layer |
| 120 | Central groove (well in some embodiments) |
| 122 | Floor of central groove |
| 130 | Graphene ribbon or sheet |

-continued

| 132 | P-type crinkle ruga in graphene ribbon |
| 134 | Central crease in crinkle |
| 136 | Nanopore on crease of graphene ribbon (2 shown) |
| 138 | electrodes |
| 140 | Plasmonic nanostructures (antenna) (2 shown) in central groove |
| 142 | Platform for plasmon antenna |
| 144 | Layer of gold or other coinage metal on graphene sheet |
| 148 | Optically transparent material on floor of central groove |
| 150 | Light aperture |
| 152 | Exit in floor of chip for electrophoretic translocation |
| 160 | Laser light source |
| 162 | Laser light beam |
| 164 | Photo detector |
| 170 | Detector array (square) |
| 172 | Detector array (circular) |
| 174 | Detector well (square) |
| 176 | Detector well (round) |
| 180 | Multilayer graphene sheet |
| 190 | Electrical lead to patch clamp amplifier |

The invention claimed is:

1. A chip for sequencing a strand of nucleic acids comprising:

a substrate fabricated from silicon or silica about 1.0 μm to about 10 μm wide, about 1.0 μm to about 10 μm long, with a thickness of about 500 nm to 2.0 μm;

wherein the substrate has a central groove about 100-500 nm wide and about 30-300 nm deep etched into the top surface of the substrate;

wherein at least one fluidic channel is provided in the floor of the groove;

wherein a multilayer graphene sheet about 1-60 nm thick is affixed to the substrate in a latitudinal orientation, with a pair of electrodes on the graphene sheet and wherein the graphene sheet is subjected to lateral compression to cause a p-type crinkle ruga having a crease to form thereon over the central groove;

wherein the graphene sheet has one or more nanopores of about 0.3 to 3.0 nm wide at the center line of the crinkle ruga crease; and a patch clamp amplifier configured to measure changes in an ionic current passing through the nanopore.

2. The chip of claim 1, further comprising a base substrate layer of silicon nitride, alumina, or boron nitride.

3. A method of detecting nucleobases in a strand of nucleic acids, comprising a chip with a graphene sheet according to claim 1, and directing a saline solution of a nucleic acid comprising a strand of nucleobases toward a nanopore in the graphene sheet, wherein the nucleobase strand translocates through the nanopore and interacts with the layers of the multilayer graphene sheet, and the patch clamp amplifier measures changes in the ionic current and detects each nucleobase in the nucleic acid strand translocating through the nanopore and the nucleic acid sequence is assigned.

4. A chip for sequencing a strand of nucleic acids comprising:

an array of wells fabricated on a silicon or silica substrate 100 to 500 μm thick, optionally having a base substrate layer of silicon nitride, alumina, or boron nitride;

wherein each well in the array of wells is about 100-500 nm wide and about 30-300 nm deep, and the wells are etched into the top surface of the silicon or silica substrate;

wherein a microfluidic channel is provided in each well that penetrates the silicon or silica substrate and base layer to form a microfluidic exit for a DNA sample;

wherein a multilayer graphene sheet 1-60 nm thick is affixed to the silicon or silica substrate, with electrodes on the graphene sheet, and wherein the graphene sheet is subjected to lateral compression to cause a P-type crinkle ruga crease to form thereon over each well;

wherein one or more nanopores about 0.3 to 3.0 nm wide are drilled into the crease of the graphene sheet over each microfluidic channel;

wherein the electrodes are configured to apply an electrical potential across the graphene sheet, to translocate a DNA sample through the nanopores in the graphene sheet and direct the DNA sample into the microfluidic exit channels.

5. The chip of claim 4, wherein the array of wells have round or square wells.

6. The chip of claim 4, wherein the array of wells comprises any combination of 3×3 to 1000×1000 wells.

*    *    *    *    *